(12) United States Patent
Chakrabarti et al.

(10) Patent No.: US 11,590,284 B2
(45) Date of Patent: Feb. 28, 2023

(54) INJECTION DEVICE

(71) Applicant: PHARMA CONSULT GES.M.B.H.

(72) Inventors: Ajoy Chakrabarti, Gaithersburg, MD (US); Eric Balsley, Darnestown, MD (US); Jacques Appy, Rives (FR); Sylvain Stamper, Saint Priest (FR); Frederic Alfonsi, Buffalo Grove, IL (US); Gaetan Painchaud, Buffalo Grove, IL (US); Nicolas Kuntzer, L'Isle d'Abeau (FR)

(73) Assignee: PHARMA CONSULT GES.M.B.H., Vienna (AT)

( * ) Notice: Subject to any disclaimer, the term of this patent is extended or adjusted under 35 U.S.C. 154(b) by 136 days.

(21) Appl. No.: 16/067,724

(22) PCT Filed: Jan. 12, 2017

(86) PCT No.: PCT/US2017/013222
§ 371 (c)(1),
(2) Date: Jul. 2, 2018

(87) PCT Pub. No.: WO2017/123783
PCT Pub. Date: Jul. 20, 2017

(65) Prior Publication Data
US 2019/0009025 A1    Jan. 10, 2019

Related U.S. Application Data

(60) Provisional application No. 62/277,939, filed on Jan. 12, 2016.

(51) Int. Cl.
*A61M 5/178* (2006.01)
*A61M 5/20* (2006.01)
(Continued)

(52) U.S. Cl.
CPC .............. *A61M 5/20* (2013.01); *A61M 5/178* (2013.01); *A61M 5/31* (2013.01); *A61M 5/315* (2013.01);
(Continued)

(58) Field of Classification Search
CPC .......... A61M 5/20; A61M 5/315; A61M 5/32; A61M 5/31571; A61M 5/31535;
(Continued)

(56) References Cited

U.S. PATENT DOCUMENTS

2005/0101919 A1*  5/2005  Brunnberg .......... A61M 5/2033
                                                      604/197
2007/0073232 A1    3/2007  Pickhard
(Continued)

FOREIGN PATENT DOCUMENTS

CA    2916317 A1    12/2014
EP    2489380 A1    8/2012
(Continued)

OTHER PUBLICATIONS

European Search Report dated Jun. 26, 2019 for corresponding European Application No. EP17 738 952.5.
(Continued)

*Primary Examiner* — Nathan R Price
*Assistant Examiner* — Tania Ismail
(74) *Attorney, Agent, or Firm* — Medler Ferro Woodhouse & Mills PLLC

(57) ABSTRACT

An autoinjector device is provided. The autoinjector device can include an activator unit including an activation housing, an activation guard, and an activation shell such that a portion of the activation guard extends beyond a proximal end of the activation shell. The autoinjector device can
(Continued)

include camouflage on a proximal surface to obscure a device lock hole and reduce user confusion around needle orientation.

10 Claims, 11 Drawing Sheets

(51) Int. Cl.
　　*A61M 5/315*　　(2006.01)
　　*A61M 5/32*　　(2006.01)
　　*A61M 5/31*　　(2006.01)
　　*A61M 5/24*　　(2006.01)
(52) U.S. Cl.
　　CPC .............. *A61M 5/32* (2013.01); *A61M 5/24* (2013.01); *A61M 5/31535* (2013.01); *A61M 5/31571* (2013.01); *A61M 2005/206* (2013.01); *A61M 2005/208* (2013.01); *A61M 2005/2026* (2013.01); *A61M 2005/2073* (2013.01); *A61M 2005/2451* (2013.01); *A61M 2005/2474* (2013.01); *A61M 2205/583* (2013.01)
(58) Field of Classification Search
　　CPC .. A61M 2005/2026; A61M 2005/2073; A61M 2005/208; A61M 2005/583; A61M 2005/2451; A61M 5/24; A61M 2005/206
　　See application file for complete search history.

(56) References Cited

U.S. PATENT DOCUMENTS

| | | |
|---|---|---|
| 2008/0097312 A1 | 4/2008 | Wilmot et al. |
| 2009/0281496 A1 | 11/2009 | Matusch |
| 2011/0125100 A1 | 5/2011 | Schwirtz et al. |
| 2013/0310759 A1 | 11/2013 | Hourmand et al. |

FOREIGN PATENT DOCUMENTS

| | | |
|---|---|---|
| JP | 2011524212 A | 9/2011 |
| WO | 2014205463 A1 | 12/2014 |

OTHER PUBLICATIONS

International Search Report dated Apr. 4, 2017 for corresponding International Application No. PCT/US2017/013222.
Written Opinion dated Oct. 14, 2020 for corresponding Singapore Application No. SG11201805322T.
Japanese Office Action dated Feb. 12, 2021 in corresponding Japanese Patent Application No. 2018-536154.

* cited by examiner

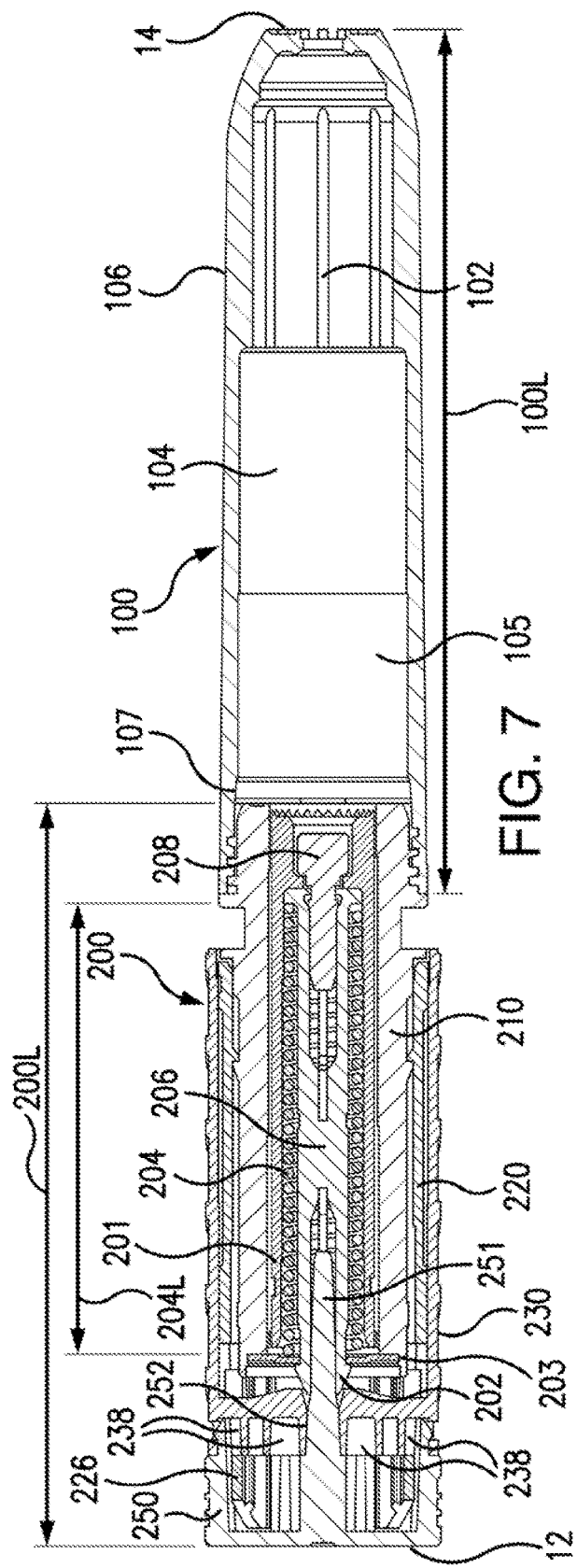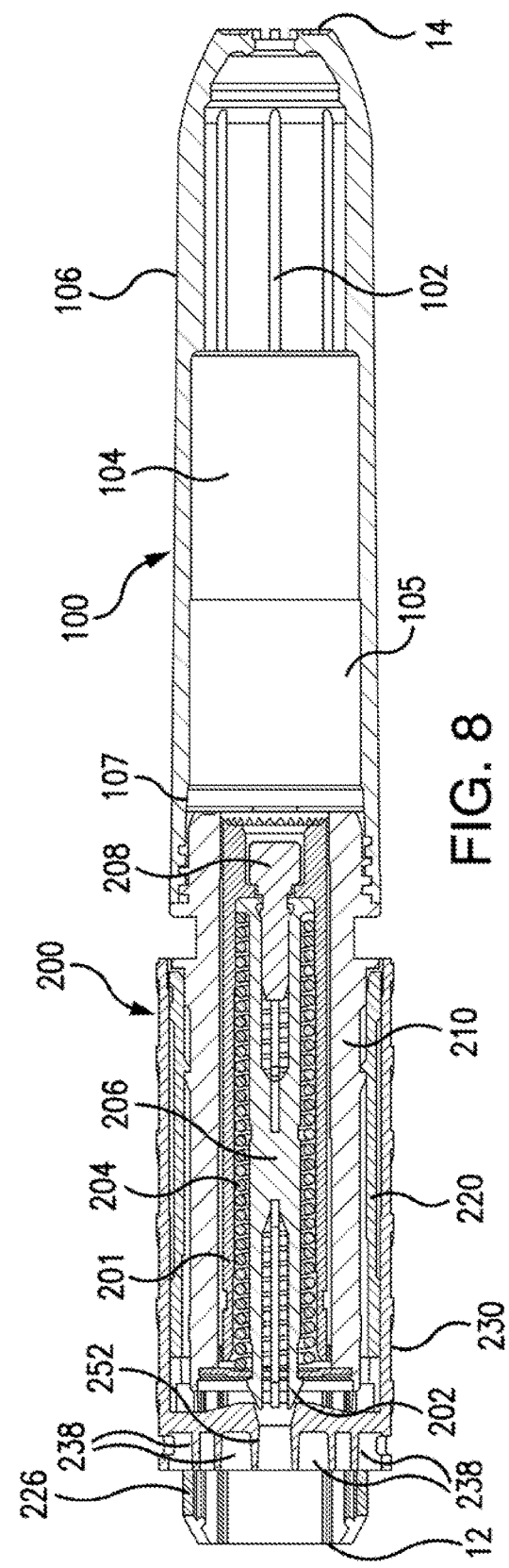

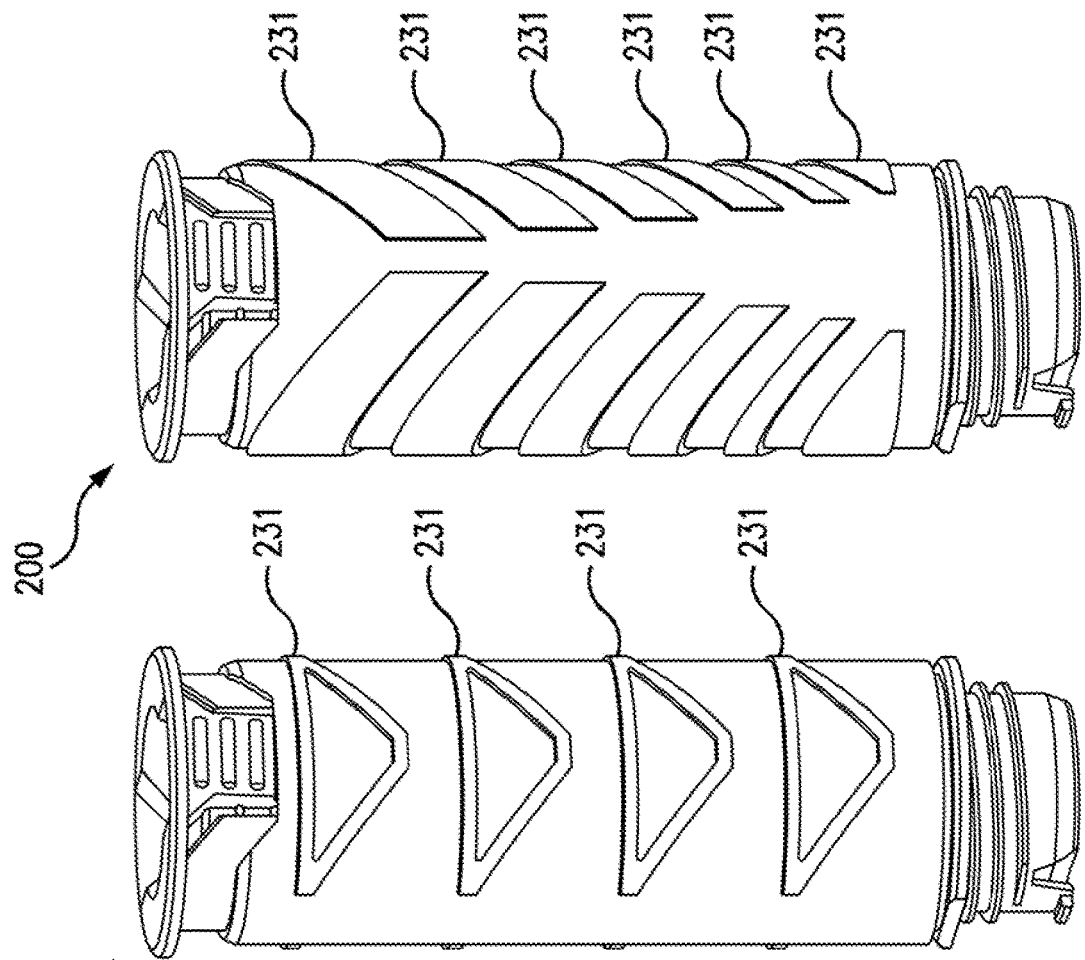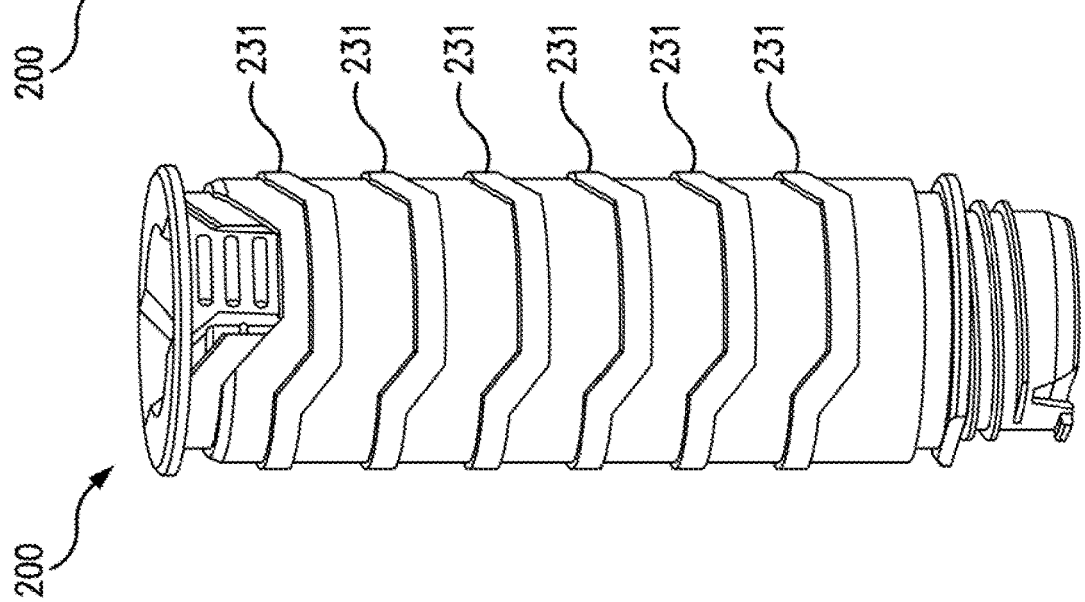

INJECTION DEVICE

BACKGROUND

Field

The invention relates generally to an activator unit for autoinjector that can include an activation guard to prevent activation of the autoinjector when the autoinjector is improperly oriented. The invention also relates to an autoinjector that can include the activator unit.

Background

Activators are components of medical hypodermic syringes that can be operated automatically, often for one-time use. Such a syringe, called an autoinjector, is placed with its distal end on a region of interest on the body of a human and is then triggered by a manual action, often in the proximal region of the autoinjector. The terms "proximal" and "distal" refer to the perspective of the person using the autoinjector. A needle extends from the distal end of the autoinjector.

Autoinjectors often administer life-saving drugs under stressful circumstances, for example, during anaphylaxis resulting from an allergic reaction or after exposure to toxic materials or chemicals. In such a scenario, a user could inadvertently invert the autoinjector risking activation of the device into the user's thumb, palm or into the air instead of into intended region of interest.

BRIEF SUMMARY OF THE INVENTION

An autoinjector device is provided that can incorporate clear instructions for use and visual and tactile cues to aide a user in properly orienting the device to reduce the frequency of device inversion. The autoinjector device can also include an activation guard to prevent activation if the autoinjector device is improperly oriented.

In one aspect of the invention, an autoinjection device can include an injection unit and an activator unit. The injector unit can be distal to the activator unit. The activator unit can include an activation housing and an activation engine positioned within an interior area of the activation housing. The activation engine can include a spring, a piston, a locking mechanism, and a retaining element. The activator unit can also include an activation guard at least partially surrounding the activation housing such that a portion of the activation housing is positioned within an interior area of the activation guard. The activation guard can extend beyond a proximal end of the activation housing. The activator unit can further include an activation shell at least partially surrounding the activation guard such that a portion of the activation guard can be positioned within an interior area of the activation shell. A portion of the activation guard can extend beyond a proximal end of the activation shell.

In an aspect, at least one of the activation housing, the activation guard, and the activation shell can be substantially cylindrical in shape. In an aspect, the activation guard can include a guard member that can extend beyond a proximal end of the activation housing.

In another aspect, the activation housing can include a radial protrusion, and the activation guard can include a groove that can at least partially surround the protrusion where the activation guard can rotate about the activation housing. In a further aspect, activation guard can include a radial protrusion, and the activation shell can include a groove surrounding the activation guard protrusion. In a further aspect, the activation shell groove can include an axial length such that the activation shell can be configured to translate about the activation guard. In another aspect, the axial length can range from approximately 2 mm to approximately 16 mm. In another aspect, the activation shell and the activation guard can be configured such that there is a relative axial rotation between them.

In a further aspect, relative axial rotation between the activation shell and the activation guard can be configured such that relative axial rotation between them is prevented.

In another aspect, the autoinjector device can include a device lock that can be configured to be positioned at a proximal end of the activation shell.

In another aspect, the device lock can include at least a radial ridge along an axial portion.

In another aspect, the activation shell can include a ridge on its outer surface.

In another aspect, the ridge can be configured to provide a user with a visual indication as to the end of the autoinjector that includes a needle. In a further aspect, a proximal surface of the activation shell can include a camouflage structure to camouflage a device lock protrusion opening. In another aspect, a distal surface of the activation guard can abut a shoulder of the activation housing.

In another aspect of the invention, an activator unit for an autoinjector can include an activation housing having an activation engine, an activation guard that can be configured about an exterior surface of the activation housing and that can extend beyond a proximal end of the activation housing, and an activation shell that can be configured about at least a portion of an exterior surface of the activation guard and that can extend beyond a proximal end of the activation shell. In another aspect, the activation housing can include at least one protrusion, and the activation guard can include a groove surrounding the at least one protrusion, such that the activation guard can rotate about the activation housing. In a further aspect, the activation guard can include at least one protrusion, and the activation shell can include at least one groove surrounding the at least one activation guard protrusion such that the activation shell can translate about the activation guard. In another aspect, a proximal surface of the activation shell can include a camouflage structure to camouflage a device lock protrusion opening. In another aspect, a distal surface of the activation guard can abut a shoulder of the activation housing. In a further aspect, the activation shell and activation guard can be configured such that relative axial rotation between them is prevented. In another aspect, the activation shell and activation guard can be configured such that they can rotate together.

In a further aspect of the invention, an activation guard for an autoinjection device to prevent a user from activating the autoinjection device in an incorrect direction, wherein the activation guard can include a guard member that can extend proximally beyond an activation housing and an activation shell, a groove configured on a portion of the guard member that can engage an activation housing projection, and a projection that can be configured on a portion of the guard member that can engage an activation shell groove. In another aspect, a portion of the activation housing can be positioned within an interior area of the activation guard, and a portion of the activation guard can be positioned within an interior area of the activation shell. In another aspect, the guard member can abut a user in the incorrect direction, and an injection unit can abut a user in a correct direction.

In another aspect of the invention, an autoinjector can include an activation shell and a device lock having a protrusion and can be configured to be positioned about a proximal end of the activation shell, where a proximal surface of the activation shell can include a camouflage structure to camouflage a device lock protrusion opening.

In another aspect of the invention, an activator unit for an autoinjector can include an activation housing including an activation guard at a proximal end of the activation housing, the activation guard can be integrally formed with the activation housing, and an activation shell that can be configured about at least a portion of an exterior surface of the activation housing, where the activation guard can extend beyond a proximal end of the activation shell.

Further features and advantages of embodiments of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to a person skilled in the relevant art based on the teachings contained herein.

BRIEF DESCRIPTION OF THE DRAWINGS/FIGURES

The accompanying drawings, which are incorporated herein and form part of the specification, illustrate embodiments of the present invention and, together with the description, further serve to explain the principles of the invention and to enable a person skilled in the relevant art to make and use the invention.

Additional features and advantages of various embodiments will be set forth, in part, in the description that follows, and will, in part, be apparent from the description, or may be learned by the practice of various embodiments. The objectives and other advantages of various embodiments will be realized and attained by means of the elements and combinations particularly pointed out in the description herein.

FIG. 7 is a sectional view of an autoinjector including a device lock according to various aspects of the invention.

FIG. 8 is a sectional view of the autoinjector device shown in FIG. 7 with the device lock removed.

FIGS. 10-12 are perspectives views of activator units according to various aspects of the invention.

Figure 1:
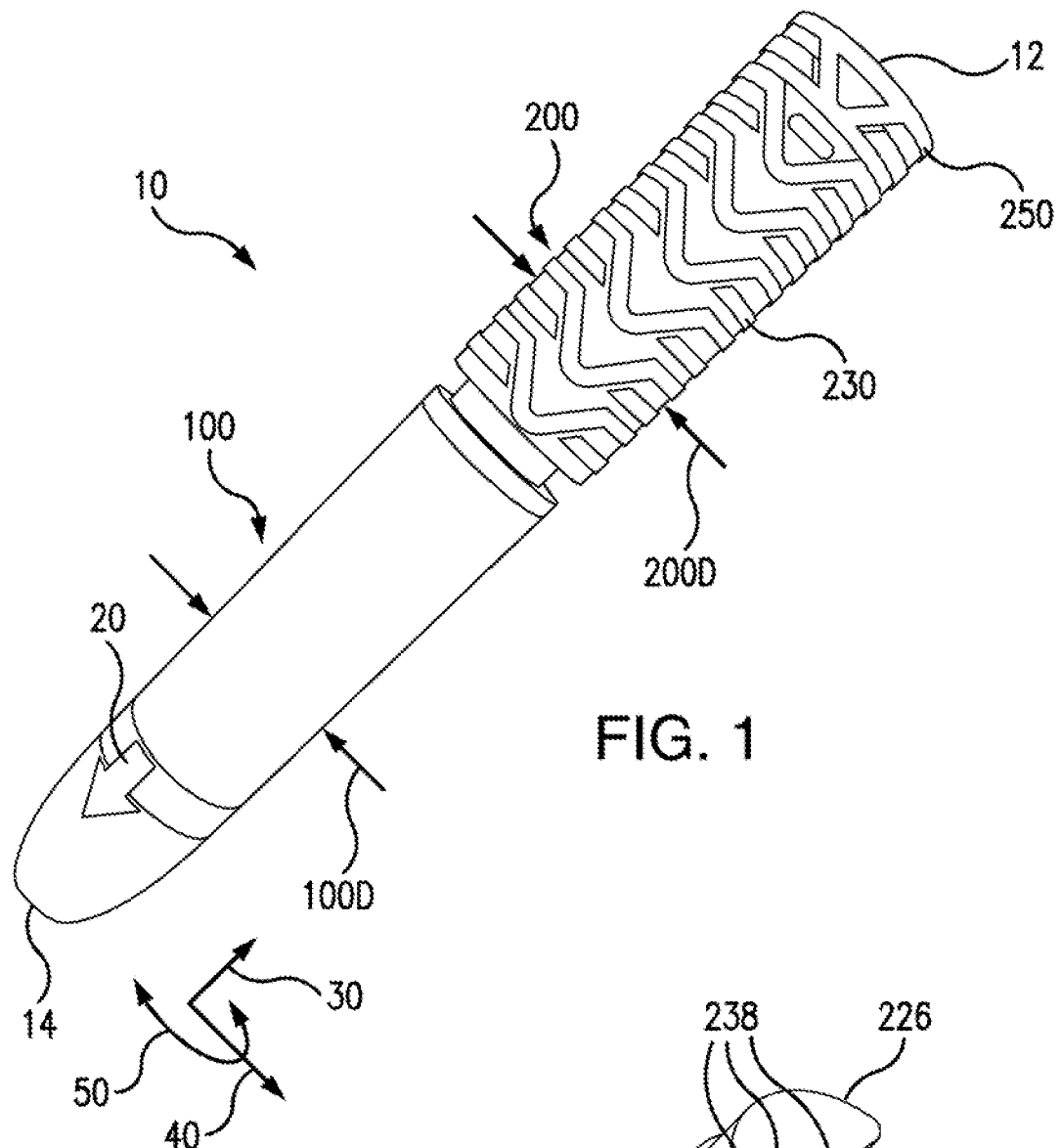
FIG. 1 is a perspective view of an autoinjector device according to various aspects of the invention.
Figure 2:
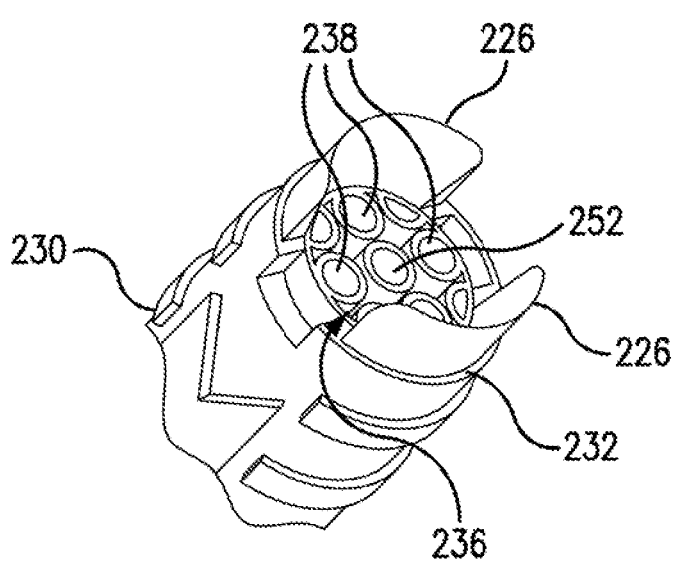
FIG. 2 is a partial perspective view of an activator unit according to various aspects of the invention.

Features and advantages of the embodiments will become more apparent from the detailed description set forth below when taken in conjunction with the drawings, in which like reference characters identify corresponding elements throughout. It is to be understood that both the foregoing general description and the following detailed description are exemplary and explanatory only, and are intended to provide an explanation of various embodiments of the present teachings.

DETAILED DESCRIPTION OF THE INVENTION

The present invention will now be described in detail with reference to embodiments thereof as illustrated in the accompanying drawings. References to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

An aspect of the present invention will now be described with reference to FIGS. 1-2 and 7-8. Medical uses for autoinjector device 10 may include, for example, administering a therapeutic injection to a patient. Axial direction 30 can run down the center of autoinjector device 10. Radial direction 40 can extend radially outward from axial direction 30. Circumferential direction 50 can encircle axial direction 30 and be tangent to radial direction 40. In an aspect of the invention, autoinjector device 10 can be symmetrical about one or more planes (i.e. reflection symmetry) or about one or more axes (i.e. rotation symmetry), such as an axis that extends along axial direction 30.

Autoinjector device 10 can have a proximal end 12 and a distal end 14. With reference to FIG. 1, autoinjector device 10 can include an injection unit 100 at its distal end 14 and an activator unit 200 at its proximal end 12. Autoinjector device 10 can include a visual indication 20 as to the end of autoinjector device 10 that includes a needle, to assist a user in properly orienting autoinjector device 10.

With reference to FIGS. 1-8, injection unit 100 can include housing 106, a storage container such as cartridge 104, a needle 102, a pressure pin 105, and a film-type seal 107.

Housing 106 can take the general shape of a cylinder, a rectangular prism, a sphere, a cube, a cone, a pyramid, or combinations thereof. In another aspect, a cross section of housing 106 can be substantially circular in shape, ovular, round, or any other shape known to one of skill in the art.

Cartridge 104 can be configured to hold one or more materials, such as liquids, gases, and/or solids. Cartridge 104 can hold a medicament, such as a pharmaceutical composition, for later delivery to a user.

Cartridge 104 can be one of many shapes or sizes, depending on the particular application. For example, cartridge 104 can take the shape of a cylinder, a rectangular prism, a sphere, a cube, a cone, a pyramid, or combinations thereof. Cartridge 104 illustrated in FIGS. 7-8, is substantially cylindrically shaped, and includes a single, central chamber. Cartridge 104 can have a total volume of, for example, of from about 0.1 to about 50 ml. In an aspect of the invention, cartridge 104 can have a total volume of, for example, 0.1 ml, 0.5 ml, 1 ml, 2 ml, 3 ml, 4 ml, 5 ml, 6 ml, 7 ml, 8 ml, 9 ml, 10 ml, 11 ml, 12 ml, 13 ml, 14 ml, 15 ml, 20 ml, 25 ml, 30 ml, 35 ml, 40 ml, 45 ml, or 50 ml.

Cartridge 104 can be made from a variety of materials. In one aspect, cartridge 104 can be glass. In another aspect, cartridge 104 can be made from one or more plastics such as, for example, polyvinylchloride, polytetrafluoroethylene, polyethersulfone, polyethylene, polyurethane, polyetherimide, polycarbonate, polyetheretherketone, polysulfone, polypropulene, cyclic olefin polymer, cyclic olefin copolymer, or combinations thereof. In an aspect, cartridge 104 can be rigid. In a further aspect, cartridge 104 can compress under the pressure of pressure pin 105.

Needle 102 can be used to pierce the user's skin and to deliver materials to the user's body. Suitable needles may include standard needles used for intradermal, subcutaneous, intramuscular, or intravenous injections, depending on the particular application.

Cartridge 104 can include a seal (not shown in the figures) at its distal end. In one example, when the autoinjector is activated, the needle 102 punctures the cartridge seal so that the needle comes in contact with the cartridge 104, such that when a pressure is applied to the cartridge 104, the medicament can flow from the cartridge 104 through the needle 102 and into the user's body. In another example, the needle 102 is pre-connected to the cartridge 104.

Cartridge 104 can include a pressure pin 105 at its proximal end. In one example, when the autoinjector is activated, a piston 208 can push the pressure pin 105 so that it moves into the cartridge 104 and creates a pressure sufficient enough for the medicament to flow from the cartridge 104 through the needle 102 and into the user's body. In another example, the piston 208 is pre-connected to the pressure pin 105.

In an aspect of the present invention, housing 106 can also include a seal-like structure, such as a film-type seal 107. In an embodiment, film-type seal 107 can be configured at the proximal end of the injection unit 100. For example, film-type seal 107 can be configured between the pressure pin 105 and the piston 208. Film-type seal 107 can include a design to maintain the sterility of the injection unit 100 even when the activator unit 200 is connected to the injection unit 100. This can be accomplished by designing the autoinjector device 10, such that a gap exists between the piston 208 and the pressure pin 105. Accordingly, the film-type seal 107 can include a thickness that can be approximately no more than the gap between the piston 208 and the pressure pin 105. For example, the film-type seal 107 can include a thickness of from about 0.001 inch or less to about 5 inches or more, from about 0.01 inch to about 1 inch, from about 0.01 inch to about 0.5 inch, or from about 0.01 inch to about 0.3 inch. Moreover, the film-type seal 107 can be made of a material that breaks when the force of the piston 208 is applied to the film-type seal 107.

Activator unit 200 can include an activator unit length 200L and the injection unit 100 can include an injection unit length 100L. The activator unit length 200L can be from about 1 inch to about 10 inches or more. For example, the activator unit length 200L can be from about 0.5 to about 8 inches, such as from about 2 to about 6 inches, from about 3 to about 4 inches, or about 3 inches. Similarly, the injection unit length 100L can be from about 1 inch to about 10 inches or more. For example, the injection unit length 100L can be from about 2 to about 8 inches, such as from about 2 to about 6 inches, from about 2.5 to about 4 inches, or about 3 inches. In one embodiment, the activator unit length 200L can be substantially the same as the injection unit length 100L. In another embodiment, the activator unit length 200L can be shorter than the injection unit length 100L. For example, the activator unit length 200L can be at least 0.1 inches shorter than the injection unit length 100L, such as about 0.1 inch, 0.2 inch, 0.3 inch, 0.4 inch, 0.5 inch, 0.6 inch, 0.7 inch, 0.8 inch, 0.9 inch, 1 inch, 1.5 inches, 2 inches, or 3 inches shorter than the injection unit length 100L. In yet another embodiment of the present invention, the activator unit length 200L can be at least 0.1 inches longer than the injection unit length 100L, such as about 0.2 inch, 0.3 inch, 0.4 inch, 0.5 inch, 0.6 inch, 0.7 inch, 0.8 inch, 0.9 inch, 1 inch, 1.5 inches, 2 inches, or 3 inches longer than the injection unit length 100L.

The activator unit 200 can include at least an activator unit diameter 200D and the injection unit 100 can include at least an injection unit diameter 100D. Activator unit diameter 200D can be from about 0.1 inch to about 3 inches or more. For example, activator unit diameter 200D can be from about 0.2 to about 2 inches, such as from about 0.3 to about 1.5 inches, from about 0.4 to about 1.4 inches, from about 0.5 to about 1.3 inches, from about 0.6 to about 1.2 inches, from about 0.7 to about 1.1 inches, or from about 0.8 to about 1 inch. The injection unit diameter 100D can be from about 0.1 inch to about 3 inches or more. For example, the injection unit diameter 100D can be from about 0.2 to about 2 inches, such as from about 0.3 to about 1 inch, from about 0.4 to about 0.8 inches, or from about 0.5 to about 0.75 inches. In one example, the distal end of the injection unit 100 has a diameter different from its proximal end. For example, the distal end of the injection unit 100 includes a diameter of from about 0.3 inches to about 0.7 inches, such as a diameter of 0.5 inches. In this example, the proximal end of the injection unit 100 includes a diameter of from about 0.6 inches to about 1 inch, for example, a diameter of 0.7 inch to about 0.9 inch, such as a diameter of about 0.8 inch.

In another embodiment of the present invention, the activator unit diameter 200D can be substantially equal to the injection unit diameter 100D. In another embodiment, the activator unit diameter 200D can be larger than the injection unit diameter 100D. For example, the activator unit diameter 200D can be at least 0.01 inches larger than the injection unit diameter 100D, such as about 0.05 inch, 0.1 inch, 0.2 inch, 0.3 inch, 0.4 inches, or 0.5 inches larger than the injection unit diameter 100D. In yet another embodiment, the activator unit diameter 200D can be smaller than the injection unit diameter 100D. For example, the activator unit diameter 200D can be at least 0.01 inches smaller than the injection unit diameter 100D, such as about 0.05 inch, 0.1 inch, 0.2 inch, 0.3 inch, 0.4 inches, or 0.5 inches smaller than the second diameter. The dimensions of the exterior of the autoinjector allows a user who is wearing protective clothing, such as a glove, to better handle and use the autoinjector 10 during an emergency situation.

The activator unit 200 can be connected to injection unit 100 by any method. For example, the activator unit 200 can be screwed, snapped, welded, glued, or friction fitted onto the injection unit 100. In one aspect of the invention, a distal portion of activator unit 200 and a proximal portion of injection unit 100 can include matching threads. In another aspect of the invention, the distal portion of the activator unit 200 and the proximal portion of injection unit 100 can include a matching tongue and groove.

Activator unit 200 can include an activation housing 210, an activation guard 220, an activation shell 230, an activation engine within activation engine housing 201, and a device lock 250.

Activation housing 210 encompasses the activation engine housing 201 having the activation engine. The activation housing can take the general shape of a cylinder, a rectangular prism, a sphere, a cube, a cone, a pyramid, or combinations thereof. In another aspect, a cross section of activation housing 210 can be substantially circular in shape, ovular, round, or any other shape known to one of skill in the art.

Activation housing 210 can be made from a variety of materials. In one aspect, activation housing 210 can be made from a metal or a metal composition. In one aspect, the activation housing 210 can be made from one or more plastics such as, for example, polyvinylchloride, polytetrafluoroethylene, polyethersulfone, polyethylene, polyurethane, polyetherimide, polycarbonate, polyetheretherketone, polysulfone, polypropulene, cyclic olefin polymer, cyclic olefin copolymer, or combinations thereof.

Activation housing 210 can have an activation housing length 210L. The activation housing length 210L can be from about 1 inch to about 10 inches or more. For example, activation housing length 210L can be from about 2 to about 8 inches, such as from about 2 to about 6 inches, from about 2 to about 4 inches, from about 2 to about 3 inches, or about 2.5 inches.

Activation housing 210 can have an activation housing diameter 210D. The activation housing diameter 210D includes a diameter that is smaller than the inner diameter of the activation guard 220 so that the activation guard 220 can be positioned such that it can cover at least a portion of the activation housing 210. In one example, the activation housing diameter 210D is from about 0.1 inch to about 3 inches or more. For example, the activation housing diameter 210D can be from about 0.2 to about 2 inches, such as from about 0.3 to about 1.5 inches, from about 0.4 to about 1.4 inches, from about 0.5 to about 1.3 inches, from about 0.6 to about 1.2 inches, from about 0.7 to about 1.1 inches, or from about 0.8 to about 1 inch.

Figure 3:
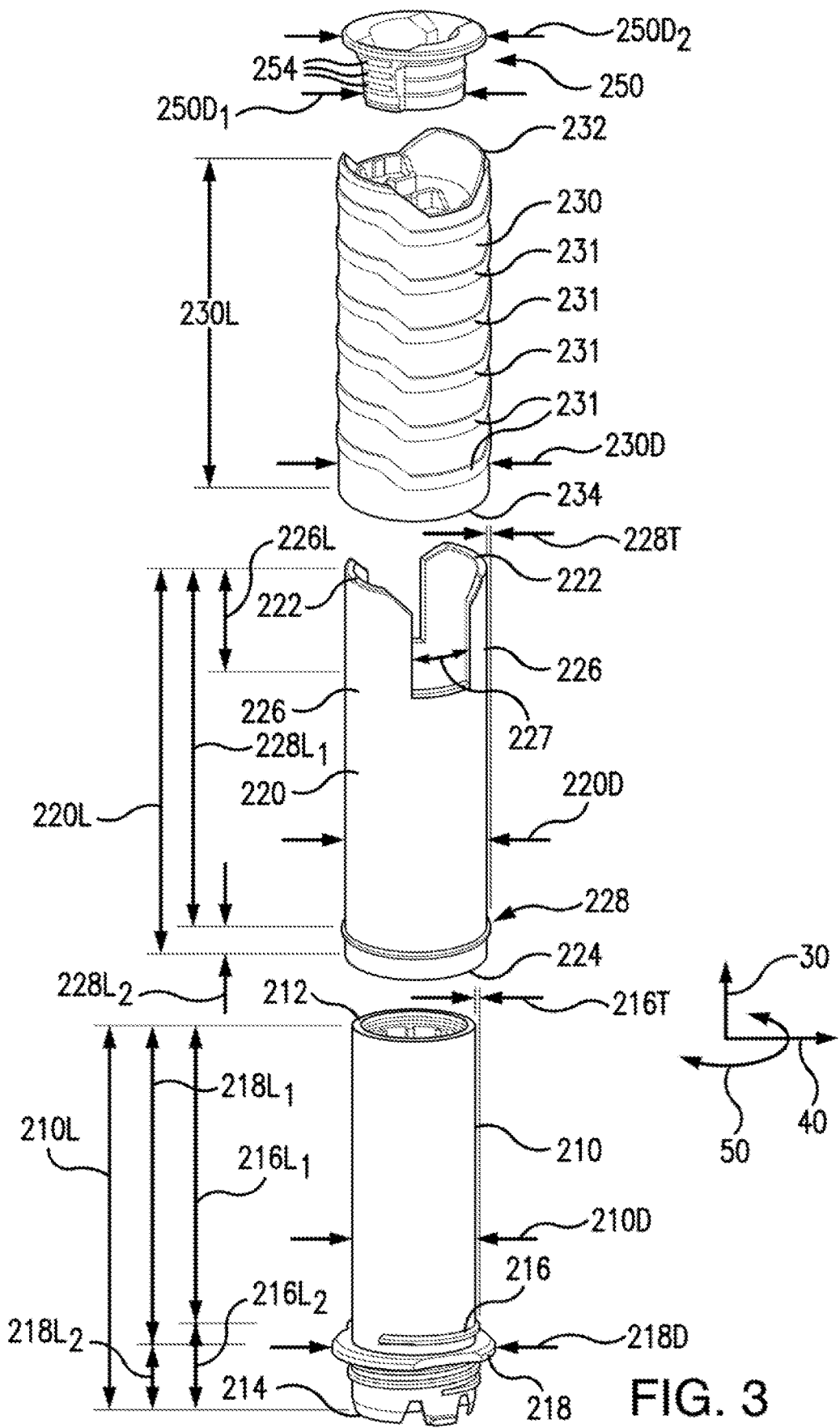
FIG. 3 is an assembly view of an activator unit according to various aspects of the invention.

Activation housing 210 can include a radial protrusion 216. The radial protrusion 216 secures the activation guard 220 and at the same time allows the activation guard 220 to circumferentially rotate around the activation housing 210. The radial protrusion 216 extends from an outer surface of activation housing 210 in radial direction 40 along at least a portion of an outer surface of activation housing 210 in circumferential direction 50. In another aspect, radial protrusion 216 can extend circumferentially along an entire outer surface of activation housing 210. The radial protrusion 216 can be positioned or formed on any portion of the activation housing 210. For example, the radial protrusion 216 can be positioned from about the distal end 214 of the activation housing 210 to about the proximal end 212 of the activation housing 210, such as the distal half of the activation housing 210, as shown in FIG. 3. Radial protrusion 216 can extend from the outer surface of activation housing 210 a protrusion thickness 216T. Protrusion thickness 216T can be from about 0.01 inch to about 1 inch or more. For example, protrusion thickness 216T can be from about 0.02 inch to 0.9 inch, from about 0.05 inch to about 0.8 inch, from about 0.1 inch to about 0.7 inch, from about 0.2 inch to about 0.6 inch, 0.3 inch to about 0.5 inch, or about 0.4 inch.

In one aspect, activation housing 210 and radial protrusion 216 can be a unitary structure manufactured as a unitary piece of material. In another aspect, radial protrusion 216 can be a discrete piece of material that is joined onto activation housing 210.

Activation housing 210 can have a first protrusion length 216L$_1$ from proximal end 212 to protrusion 216 in the axial direction. First protrusion length 216L$_1$ can be from about 1 inch to about 16 inches or more. For example, first protrusion length 216L$_1$ can be from about 1 to about 8 inches, such as from about 1.5 to about 6 inches, from about 1.5 to about 4 inches, from about 1.5 to about 3 inches, or about 1.8 inches.

Activation housing 210 can have a second protrusion length 216L$_2$ from distal end 214 to protrusion 216 in the axial direction. Second protrusion length 216L$_2$ can be from about 0.1 inch to about 10 inches or more. For example, second protrusion length 216L$_2$ can be from about 0.3 to about 5 inches, such as from about 0.5 to about 1.5 inches, from about 0.6 to about 1 inch, from about 0.7 to about 0.9 inches, or about 0.8 inches.

Figure 4:
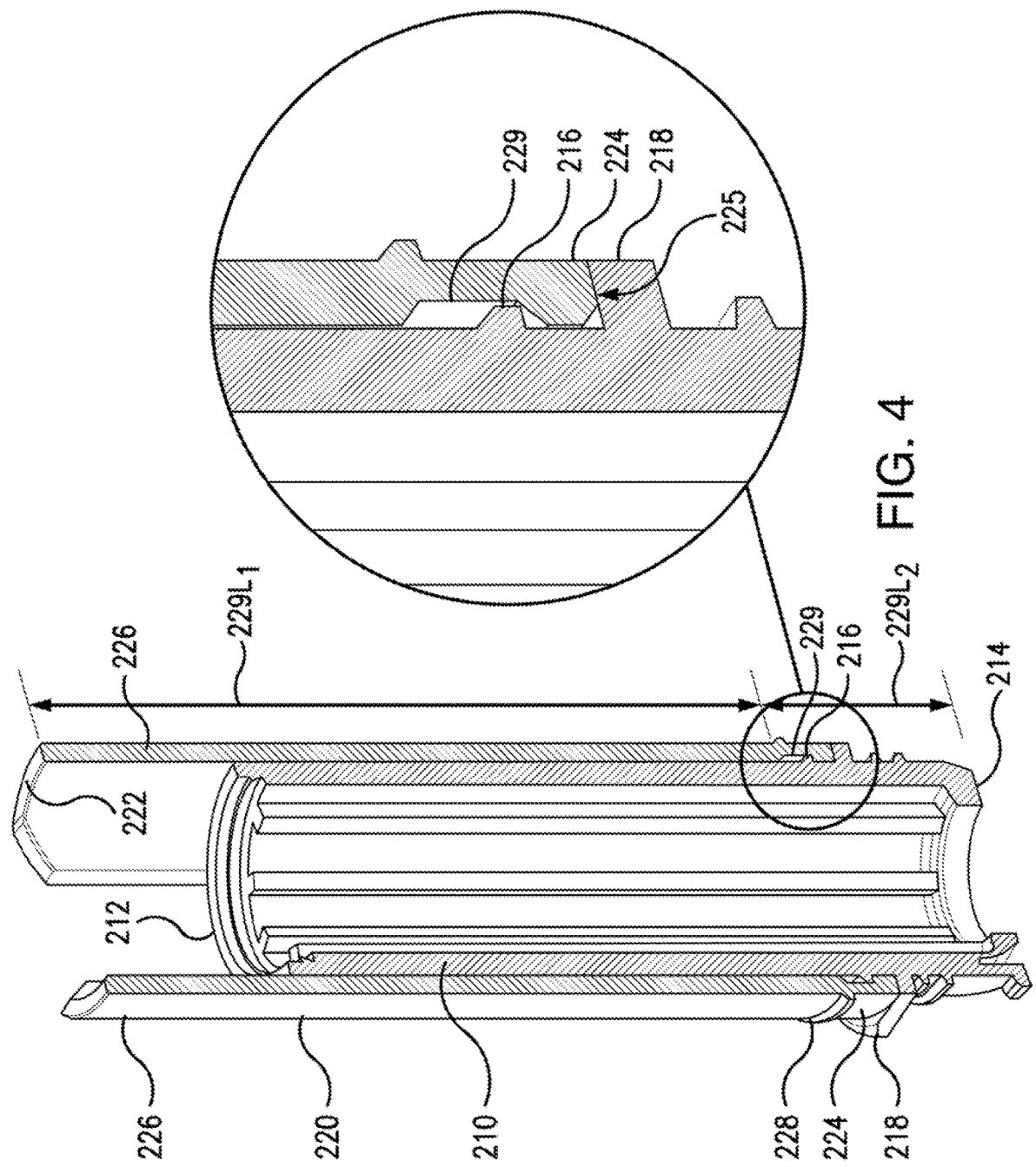
FIG. 4 is a sectional view of an activation housing and activation guard according to various aspects of the invention.

Activation housing 210 can include a shoulder 218 that can be positioned or formed on any portion of the activation housing 210. For example, the shoulder 218 can be positioned from about the distal end 214 of the activation housing 210 to about the proximal end 212 of the activation housing 210, such as the distal half of the activation housing 210. In one example, the shoulder is positioned or formed below or distal to the radial protrusion 216, as shown in FIG. 4. The shoulder 218 can be positioned adjacent distal end 224 of activation guard such that activation guard distal surface 225 abuts the surface of shoulder 218. Shoulder 218 can extend outward from the outer surface of activation housing 210 in radial direction 40 along at least a portion of an outer surface of activation housing 210 in circumferential direction 50. In another aspect, shoulder 218 can extend outward and circumferentially along an entire outer surface of activation housing 210.

In one aspect, activation housing 210 and shoulder 218 can be a unitary structure manufactured as a unitary piece of material. In another aspect, shoulder 218 can be a discrete piece of material that is joined onto activation housing 210.

Shoulder 218 can have a shoulder diameter 218D. Shoulder diameter 218D can be from about 0.1 inch to about 2 inches or more. For example, the shoulder diameter 218D can be from about 0.2 to about 2 inches, such as from about 0.3 to about 1.5 inches, from about 0.4 to about 1.4 inches, from about 0.5 to about 1.3 inches, from about 0.6 to about 1.2 inches, from about 0.7 to about 1.1 inches, or from about 0.8 to about 1 inch. Shoulder diameter 218D can be larger than activation housing diameter 210D. For example, shoulder diameter 218D can be at least 0.01 inches larger than activation housing diameter 210D, such as about 0.1 to about 0.2 inches larger than the activation housing diameter 210D.

Activation housing 210 can have a first shoulder length 218L$_1$ from proximal end 212 to shoulder 218 in the axial direction. First shoulder length 218L$_1$ can be from about 1 inch to about 10 inches or more. For example, first shoulder length 218L$_1$ can be from about 1.5 to about 6 inches, such as from about 1.5 to about 3 inches, from about 1.5 to about 2.5 inches, or about 2 inches.

Activation housing 210 can have a second shoulder length 218L$_2$ from distal end 214 to shoulder 218 in the axial direction. Second shoulder length 218L$_2$ can be from about 1 inch to about 10 inches or more. For example, second shoulder length 218L$_2$ can be from about 0.1 to about 1 inches, such as from about 0.2 to about 0.9 inches, from about 0.3 to about 0.8 inches, from about 0.4 to about 0.7 inches, or about 0.5 to about 0.6 inches.

Activator unit 200 can include an activation guard 220. Activation guard 220 can take the general shape of a cylinder, a rectangular prism, a sphere, a cube, a cone, a pyramid, or combinations thereof. In another aspect, a cross section of activation guard 220 can be substantially circular in shape, ovular, round, or any other shape known to one of skill in the art. Activation guard 220 can be made from a variety of materials. In one aspect, activation guard 220 can be made from one or more plastics such as, for example, polyvinylchloride, polytetrafluoroethylene, polyethersulfone, polyethylene, polyurethane, polyetherimide, polycarbonate, polyetheretherketone, polysulfone, polypropulene, cyclic olefin polymer, cyclic olefin copolymer, or combinations thereof.

Activation guard 220 can extend beyond a proximal end of an activation shell 230. When autoinjector device 10 is improperly oriented, e.g., when proximal end 12 is positioned adjacent a user, activation guard 220 abuts the user and prevents the activation shell 230 from contacting the user and activating the autoinjector device 10.

Activation guard 220 can have an activation guard length 220L and is positioned such that a portion of it extends beyond the proximal end of the activation housing 210 and the activation shell 230. The activation guard length 220L can be from about 1 inch to about 10 inches or more. For example, activation guard length 220L can be from about 1 to about 6 inches, such as from about 2 to about 4 inches, from about 2 to about 3 inches, or about 2.5 inches. In one embodiment of the present invention, the activation guard length 220L can be substantially the same as the activation housing length 210L. In another embodiment of the present invention, the activation guard length 220L can be shorter than the activation housing length 210L. For example, the activation guard length 220L can be at least 0.1 inches shorter than the activation housing length 210L, such as about 0.5 inch, 0.75 inch, 1 inch, 1.5 inches, 2 inches, 2.5 inches, 3 inches, 3.5 inches, 4 inches, 4.5 inches, or 5 inches shorter than the activation housing length 210L. In yet another embodiment of the present invention, activation guard length 220L can be at least 0.1 inches longer than the activation housing length 210L, such as about 0.5 inch, 0.75 inch, 1 inch, 1.5 inches, 2 inches, 2.5 inches, 3 inches, 3.5 inches, 4 inches, 4.5 inches, or 5 inches longer than the activation housing length 210L.

Activation guard 220 can have an activation guard diameter 220D. The activation guard diameter 220D. The activation guard diameter 220D is larger than the activation housing diameter 210D so that it can slide over the activation housing 210 and smaller than an activation shell diameter 230D. The activation housing diameter 220D can be from about 0.1 inch to about 3 inches or more. For example, the activation guard diameter 220D can be from about 0.2 to about 2 inches, such as from about 0.3 to about 1.5 inches, from about 0.4 to about 10 inch, from about 0.5 to about 0.8 inches, from about 0.6 to about 0.8 inches, from about 0.7 to about 0.8 inches.

Figure 6:
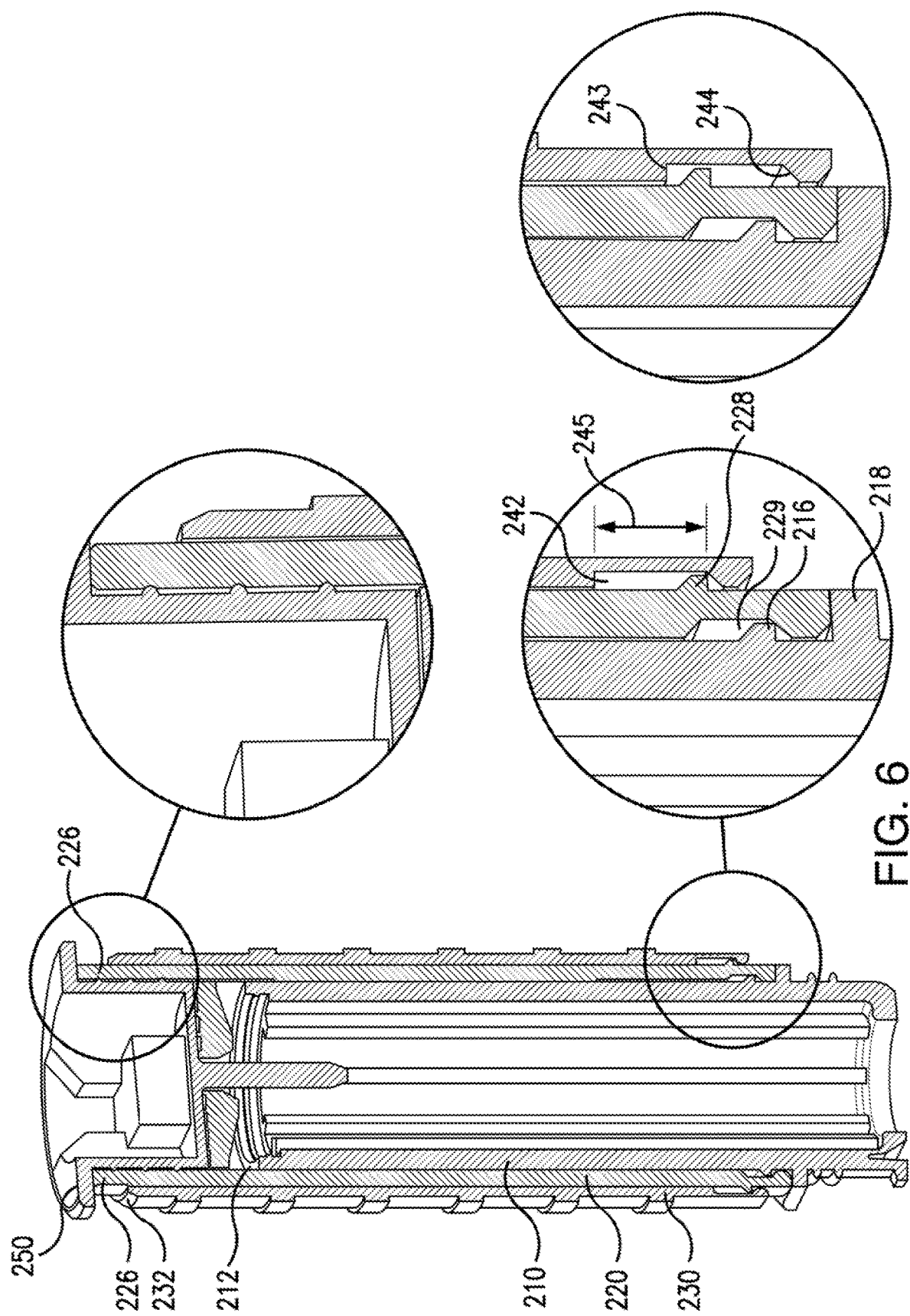
FIG. 6 is a sectional view of an activation housing, activation guard, activation shell, and device lock according to various aspects of the invention.

Activation guard 220 can include a radial protrusion 228. The radial protrusion 228 secures the activation shell 230 and at the same time allows the activation shell 230 to move axially so that it can activate the autoinjector 10. The radial protrusion 228 extends outward along radial direction 40 along at least a portion of an outer surface of activation guard 220 in circumferential direction 50. In another aspect, radial protrusion 228 can extend circumferentially along an entire outer surface of activation guard 220. The radial protrusion 228 can be positioned or formed on any portion of the activation guard 220. For example, the radial protrusion 228 can be positioned from about the distal end of the activation guard 220 to about the proximal end of the activation guard 220, such as the distal half of the activation guard 220, as shown in FIGS. 4 and 6. Radial protrusion 228 can extend from the outer surface of activation housing 210 a protrusion thickness 228T. Protrusion thickness 228T can be from about 0.01 inch to about 1 inch or more. For example, protrusion thickness 228T can be from about 0.02 inch to 0.9 inch, from about 0.05 inch to about 0.2 inch, or from about 0.05 inch to about 0.1 inch.

In one aspect, activation guard 220 and radial protrusion 228 can be a unitary structure manufactured as a unitary piece of material. In another aspect, radial protrusion 228 can be a discrete piece of material that is joined onto activation guard 220.

Activation guard 220 can have a first protrusion length $228L_1$ from proximal end 222 to protrusion 228 along the axial direction. First protrusion length $228L_1$ can be from about 1 inch to about 10 inches or more. For example, first protrusion length $228L_1$ can be from about 1 to about 6 inches, such as from about 2 to about 4 inches, from about 2 to about 3 inches, from about 2.0 to about 2.5 inches, or about 2.3 inches.

Activation guard 220 can have a second protrusion length $228L_2$ from distal end 224 to protrusion 228 along the axial direction. Second protrusion length $228L_2$ can be from about 0.01 inch to about 10 inches or more. For example, second protrusion length $228L_2$ can be from about 0.05 to about 1 inch, such as from about 0.07 to about 0.5 inches, from about 0.07 to about 0.3 inches, or from about 0.08 to about 0.2 inches.

Activation guard 220 can have a groove 229 that interacts or engages the radial protrusion 216. The groove 229 extends radially into an interior surface of activation guard 220 along at least a portion of the interior surface of activation guard 220 in circumferential direction 50. Groove 229 can have a depth from approximately 0.01 or less to approximately 0.1 inch or more. In one aspect, groove 229 can extend circumferentially along an entire interior surface of activation guard 220. In another aspect, groove 229 can extend along a portion of the interior surface of the activation guard 220.

Activation guard 220 can have a first groove length $229L_1$ from proximal end 222 to groove 229 along the axial direction. First groove length $229L_1$ can be from about 1 inch to about 16 inches or more. For example, first groove length $229L_1$ can be from about 1.5 to about 3 inches, such as from about 1.5 to about 2.5 inches, or from about 2 to about 2.4 inches.

Activation guard 220 can have a second groove length $229L_2$ from distal end 224 to groove 229 along the axial direction. Second groove length $229L_2$ can be from about 0.1 inch to about 10 inches or more. For example, second groove length $229L_2$ can be from about 0.5 to about 2 inches, such as from about 0.6 to about 1 inch, or from about 0.7 to about 0.9 inch.

In one aspect of the invention, activation guard 220 can include one or more guard members 226, positioned at proximal end 222 of activation guard 220. In one aspect, activation guard 220 and guard members 226 can be a unitary structure manufactured as a unitary piece of material. In one aspect, the guard member 226 may be simply the proximal portion of the activation guard 220 that extends beyond the activation housing 210 and the activation shell

230. In one example, the guard members 226 include a gap 227, thus forming one or more guard members 226. The gap 227 can extend along circumferential direction 50. Gap 227 can have any length and width. For example, gap 227 can include a length of about 0.25 inch. In another aspect, guard members 226 can be curved along circumferential direction 50 and can a have a radius of curvature. For example, guard members 226 can have a radius of curvature of from about 0.2 to about 0.5 inch. In an alternate aspect of the invention, guard member 226 can be straight and can be beam shaped, as shown, for example, in FIGS. 15-16. In another aspect, guard members 226 can be discrete pieces of material that are joined onto activation guard 220. In another aspect of the invention, one or more guard members 226 can be integrally formed with activation housing 210 at its proximal end 212 and can extend beyond proximal end 232 of activation shell 230.

Guard members 226 can have a guard member length 226L from proximal end 222 toward distal end 224 along the axial direction. The guard member length 226L includes a length sufficient so that that when the guard member 226 comes in contact with a user's body, it can prevent the activation shell 230 from moving, thus activating the autoinjector 10. In one example, the guard member length 226L can be from about 0.1 inch to about 2 inches or more. For example, guard member length 226L can be from about 0.2 to about 1 inch, such as from about 0.3 to about 0.9 inches, from about 0.3 to about 0.8 inches, from about 0.3 to about 0.5 inches, or about 0.4 inches.

Activation of an improperly oriented device without a suitable activation guard could prevent delivery of the drug within the autoinjector device 10 to the intended region of interest of a user and could even result in unwanted activation of needle 102 into a user's thumb. Activation guard 220 and guard members 226 can prevent the activation shell 230 from contacting a user and moving toward distal end 14 to activate an improperly oriented autoinjector device 10. For example, when improperly oriented proximal end 12 of autoinjector device 10 and activation guard proximal end 222 can abut a user and distal end 14 containing a needle can extend away from the user. Activation guard 220 is attached to activation housing 210 to prevent linear translation of activation guard 220 with respect to activation housing 210. Applying a linear force to autoinjector device 10 when activation guard members 226 abut a user will therefore not activate autoinjector device 10 to extend needle 102.

Activator unit 200 can include an activation shell 230. Activation shell 230 when moved by a user in an axial direction toward distal end 14 activates the autoinjector 10. The activation shell 230 can take the general shape of a cylinder, a rectangular prism, a sphere, a cube, a cone, a pyramid, or combinations thereof. In another aspect, a cross section of activation shell 230 can be substantially circular in shape, ovular, round, or any other shape known to one of skill in the art.

Activation shell 230 can be made from a variety of materials. In one aspect, activation shell 230 can be made from one or more plastics such as, for example, polyvinylchloride, polytetrafluoroethylene, polyethersulfone, polyethylene, polyurethane, polyetherimide, polycarbonate, polyetheretherketone, polysulfone, polypropulene, cyclic olefin polymer, cyclic olefin copolymer, or combinations thereof.

Activation shell 230 can have an activation shell length 230L. The activation shell length 230L can be from about 1 inch to about 10 inches or more. For example, activation shell length 230L can be from about 1 to about 6 inches, such as from about 1 to about 3 inches, from about 2 to about 3 inches, or from about 2 to about 2.5 inches. In one embodiment of the present invention, the activation shell length 230L can be shorter than the activation guard length 220L. For example, the activation shell length 230L can be at least 0.1 inches shorter than the activation guard length 220L, such as about 0.3 inch, 0.4 inch, 0.5 inch, or 1 inch shorter than the activation guard length 220L.

Activation shell 230 can have an activation shell diameter 230D. The activation shell diameter 230D is larger than the activation guard diameter 220D so that it can slide over the activation guard 220. The activation shell diameter 230D can be from about 0.1 inch to about 3 inches or more. For example, the activation shell diameter 230D can be from about 0.2 to about 2 inches, such as from about 0.3 to about 1.5 inches, from about 0.4 to about 1.2 inches, from about 0.5 to about 1.1 inches, from about 0.6 to about 1 inch, from about 0.7 to about 1 inch, or from about 0.8 to about 1 inch.

In one aspect of the invention, activation shell 230 can include a distal groove 242 that can extend radially into at least a portion of an interior surface of activation shell 230 along circumferential direction 50. In one aspect, distal groove 242 can extend into an interior surface of activation shell 230 along an entire interior surface of activation shell 230.

Distal groove 242 can have an axial length 245 between the groove proximal end 243 and the groove distal end 244 to allow for activation of autoinjector device 10. For example, axial length 245 interacts with or engages the radial protrusion 228 to permit translation of activation shell 230 about activation guard 220 and activation housing 210 to activate autoinjector device 10. In one aspect of the invention, axial length 245 can be approximately 0.1. In another aspect, axial length 245 can range from approximately 0.1 to approximately 0.2 inch.

Activation shell 230 can be prevented from moving toward proximal end 12 of autoinjector device 10, for example when proximal end 12 abuts a user, because distal end 244 of distal groove 242 abuts radial protrusion 228. The positioning of distal end 244 against radial protrusion 228 only allows activation shell 230 to move toward distal end 14 for activation of autoinjector device 10. This configuration therefore prevents a user from grasping activation shell 230 to apply a linear force and activate autoinjector device 10 when autoinjector device 10 is in an improper orientation, e.g., when proximal end 12 abuts a user at the intended injection site.

In an aspect, activation guard 220 can be omitted and axial length 245 of distal groove 242 can interact with a radial protrusion on activation housing 210. For example, shoulder 218 can be omitted and distal groove 242 can interact with radial protrusion 216. In this aspect, proximal end 212 of activation housing 210 can extend beyond proximal end 232 of activation shell 230.

Distal groove 242 can have a depth from approximately 0.01 to approximately 0.2 inch.

Figure 5:
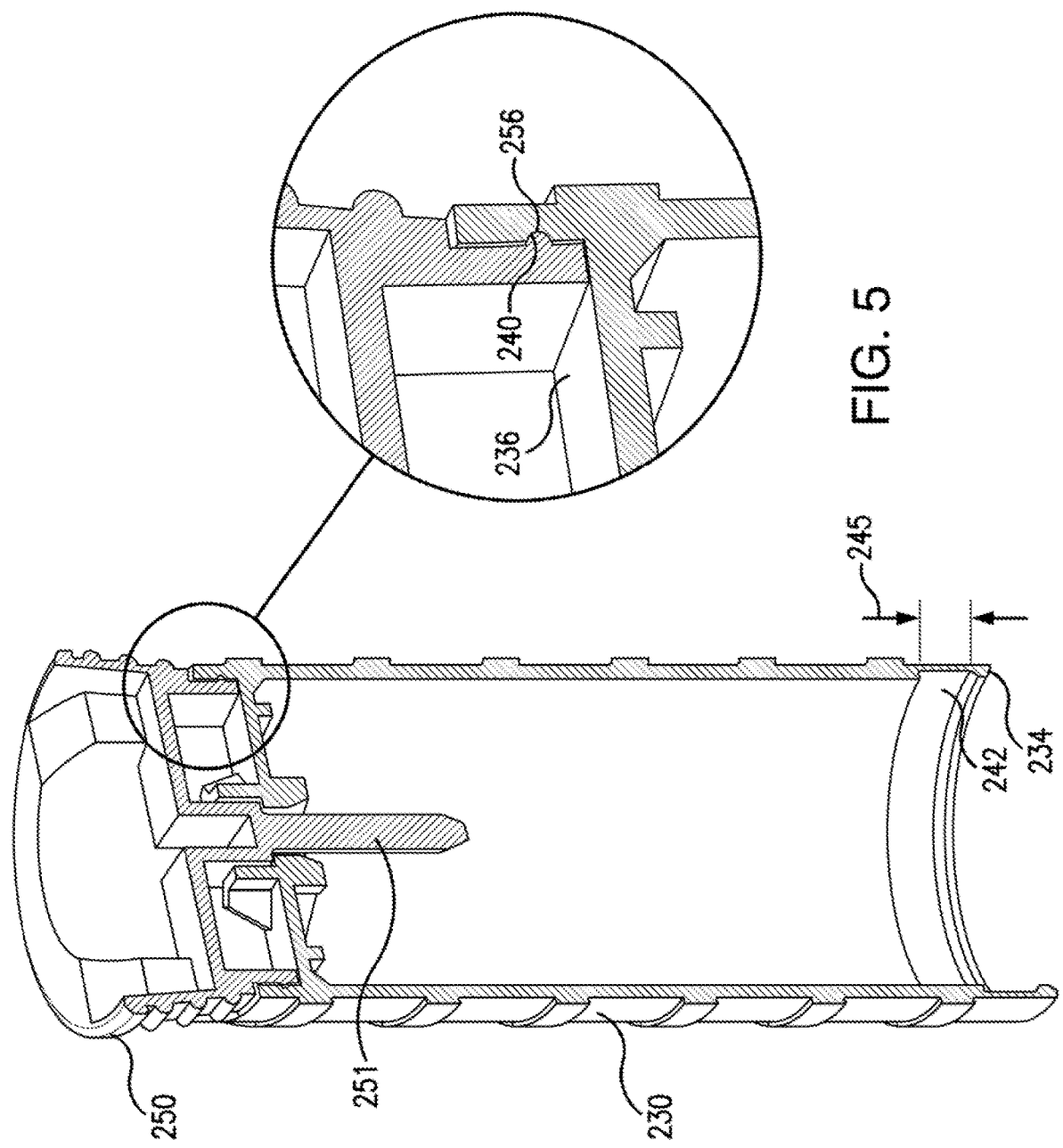
FIG. 5 is a sectional view of an activation shell and device lock according to various aspects of the invention.

In another aspect, activation shell 230 can include a proximal grove 240 that is configured to couple with a radial protrusion 256 on device lock 250 to hold device lock 250 in place on activation shell 230 (FIG. 5). Proximal groove 240 can have a groove depth of about 0.01 to about 0.2 inch. In another aspect, the groove 240 is an opening and the radial protrusion 256 is a hook or a clip that can secure the device lock 250 to the activation shell. In yet another aspect, the groove 240 is female thread and the radial protrusion 256 is a male thread. In this aspect, the device lock 250 can be threaded on to the activation shell 230, thereby securing the device lock 250 onto the activation shell 230.

Activation shell 230 can include one or more protrusions 231. As illustrated in FIG. 3, protrusions 231 can add texture to the outer surface of activation shell 230 to increase a user's ability to grip and hold activator shell 230. In another aspect, protrusions 231 can provide a visual indication as to the end of autoinjector device 10 that includes a needle, to assist a user in properly orienting autoinjector device 10. As shown in FIGS. 1, 3, and 10-12, the downward or distal direction can be visually indicated by the pattern of protrusions 231. For example, protrusions 231 can include a V shape (FIG. 1), a U shape (FIGS. 3 and 10), a triangle shape (FIG. 11), or a curved bar shape (FIG. 12). Protrusions 231 can also include a directional texture to provide a tactile indication as to the end of autoinjector device 10 that includes a needle, to assist a user in properly orienting autoinjector device 10 in the dark.

Proximal surface 236 of activation shell 230 can include camouflage to obscure device lock hole 252 and reduce user confusion around needle orientation. In an aspect, proximal surface 236 of activation shell 230 can include one or more camouflage structures 238. Camouflage structures 238 are structural devices to camouflage and obscure device lock hole 252 and reduce user confusion around needle orientation. For example, without camouflage structures 238, proximal end 12 and distal end 14 each include a single hole: device lock hole 252 at proximal end 12 and a hole through which needle 102 extends at distal end 14. A user might therefore confuse device lock hole 252 with the needle hole, resulting in an improper orientation (e.g. inversion) of autoinjector device 10 where proximal end 12 abuts a user at the intended injection site, instead of distal end 14. Camouflage structures 238 obscure device lock hole 252 and prevent a user from thinking device lock hole 252 is the needle hole. Camouflage structures 238 can be apertures that extend through proximal surface 236. In another aspect, camouflage structures 238 can be indentations extending distally into proximal surface 236. In another aspect, camouflage structures 238 can be protrusions extending proximally from proximal surface 236. Camouflage structures 238 can take the shape of a cylinder, a rectangular prism, a sphere, a cube, a cone, a pyramid, or combinations thereof. In another aspect, proximal surface 236 can include non-structural camouflage to camouflage and obscure device lock hole 252 and reduce user confusion around needle orientation. For example, proximal surface 236 can be colored, for example, using paint, stickers, or other non-structural features. In an aspect, proximal surface 236 can be colored black to obscure device lock hole 252.

Activator unit 200 can include a device lock 250. Device lock 250 can take the general shape of a cylinder, a rectangular prism, a sphere, a cube, a cone, a pyramid, or combinations thereof. In another aspect, a cross section of device lock 250 can be substantially circular in shape, ovular, round, or any other shape known to one of skill in the art.

Device lock 250 can be made from a variety of materials. In one aspect, device lock 250 can be made from one or more plastics such as, for example, polyvinylchloride, polytetrafluoroethylene, polyethersulfone, polyethylene, polyurethane, polyetherimide, polycarbonate, polyetheretherketone, polysulfone, polypropulene, cyclic olefin polymer, cyclic olefin copolymer, or combinations thereof.

Device lock 250 can have a first device lock diameter $250D_1$ at its distal end. The first device lock diameter $250D_1$ can be from about 0.1 inch to about 1.5 inches or more. For example, the first device lock diameter $250D_1$ can be from about 0.2 to about 1.4 inches, such as from about 0.3 to about 1.3 inches, from about 0.4 to about 1.2 inches, from about 0.5 to about 1.1 inches, from about 0.6 to about 1 inch, from about 0.7 to about 0.9 inch, or about 0.8 inch. In another embodiment, the first device lock diameter $250D_1$ can be smaller than activation shell diameter 230D. For example, the first device lock diameter $250D_1$ can be at least 0.01 inches smaller than the activation shell diameter 230D, such as about 0.05 inch, 0.1 inch, 0.2 inches, or 0.3 inches smaller than the activation shell diameter 230D.

Device lock 250 can have a second device lock diameter $250D_2$ at its proximal end. The second device lock diameter $250D_2$ can include a diameter that is substantially similar to the activation shell diameter 230D. For example, the second device lock diameter $250D_2$ can be from about 0.1 inch to about 3 inches or more. For example, the second device lock diameter $250D_2$ can be from about 0.2 to about 2 inches, such as from about 0.3 to about 1.5 inches, from about 0.4 to about 1.4 inches, from about 0.5 to about 1.3 inches, from about 0.6 to about 1.2 inches, from about 0.7 to about 1.1 inches, or from about 0.8 to about 1 inch. In another embodiment, the second device lock diameter $250D_2$ can be equal to or larger than activation shell diameter 230D. For example, the second device lock diameter $250D_2$ can be at least 0.1 inch larger than the activation shell diameter 230D, such as about 0.2 inch, 0.3 inch, 0.4 inches, or 0.5 inch larger than the activation shell diameter 230D.

Device lock 250 can include a central pin 251 that extends into activator unit 200 to prevent the autoinjector 10 from unwanted activation. Central pin 251 can have a pin length (not shown) sufficient to reach detent projections 202 of the retaining element 206. Central pin 251 can have a pin length of from about 0.5 inch to about 2 inches or more. For example, pin length can be from about 0.6 to about 1.5 inches, such as from about 0.7 to about 1 inch, or from about 0.8 to about 0.9 inch inches.

Device lock 250 can include one or more radial protrusions 254 positioned along an axial length of device lock 250 to increase the grip and friction between device lock 250 and a user's fingers. Radial protrusions 254 can make it easier for a user to grip and remove device lock 250 from autoinjector device 10, especially under low visibility conditions.

Activator unit 200 can include an activation engine including activation engine housing 201 that can include a pushing mechanism 204 that can propel piston 208 through film-type seal 107 into pressure pin 105 to force needle 102 through distal end 14 of autoinjector device 10. In some embodiments, the needle 102 can puncture the cartridge seal so that the needle 102 comes in contact with the cartridge 104 and the medicament in the cartridge 104. In one aspect of the invention, pushing mechanism 204 can be motorized and can include an electric motor, a pneumatic motor, or a hydraulic motor coupled to piston 208. In another aspect, pushing mechanism 204 can be non-motorized and can include a mechanical energy storage device such as a spring or compressed air. For example, pushing mechanism 204 can be a compression spring, an extension spring, a torsion spring, a constant force spring, a variable force spring, or a coil spring. The spring can include a design to enable the pushing mechanism 204 to exert sufficient force to pierce the skin of the user and inject the contents of cartridge 104 into the user. For example, the spring can include a design to enable the pushing mechanism 204 to assert a pressure of from about 10 psi or less to about 1000 psi or more to the content of the cartridge 104. For example, the pushing mechanism 204 asserts a pressure of from about 60 psi to about 500 psi, from about 80 psi to about 350 psi, from about 180 psi to about 330 psi. In one aspect, the pressure is a constant pressure. In another aspect, the initial pressure is greater than the final pressure.

In one aspect of the invention, activation guard 220 can be positioned to at least partially surround the activation housing 210, such that a portion of activation housing 210 can be positioned within an interior area of activation guard 220. In a further aspect, activation guard 220 can at least partially surround an exterior surface of activation housing 210. In one aspect of the invention, distal end 224 of activation guard can be positioned adjacent to shoulder 218 such that activation guard distal surface 225 abuts the surface of shoulder 218. Groove 229 can at least partially surround a radial protrusion 216 that extends along at least a portion of an outer surface of activation housing 210 in circumferential direction 50. Radial protrusion 216 can extend circumferentially along an entire outer surface of activation housing 210. In one aspect, groove 229 and radial protrusion 216 can permit rotation of activation guard 220 about activation housing 210. This aspect will prevent a user from twisting the activator unit 200 in relation to the injection unit 100 to separate the two parts and disassemble the autoinjector 10. Groove 229 and radial protrusion 216 can prevent axial translation between activation housing 210 and activation guard 220.

In one aspect of the invention, activation shell 230 can be positioned at least partially surrounding an activation housing 210, such that a portion of activation housing 210 can be positioned within an interior area of activation shell 230. In a further aspect, activation shell 230 can at least partially surround an exterior surface of activation housing 210. Activation shell 230 can be moved towards the distal end of activator unit 200 and distal end 14 of autoinjector device 10.

Figure 13:
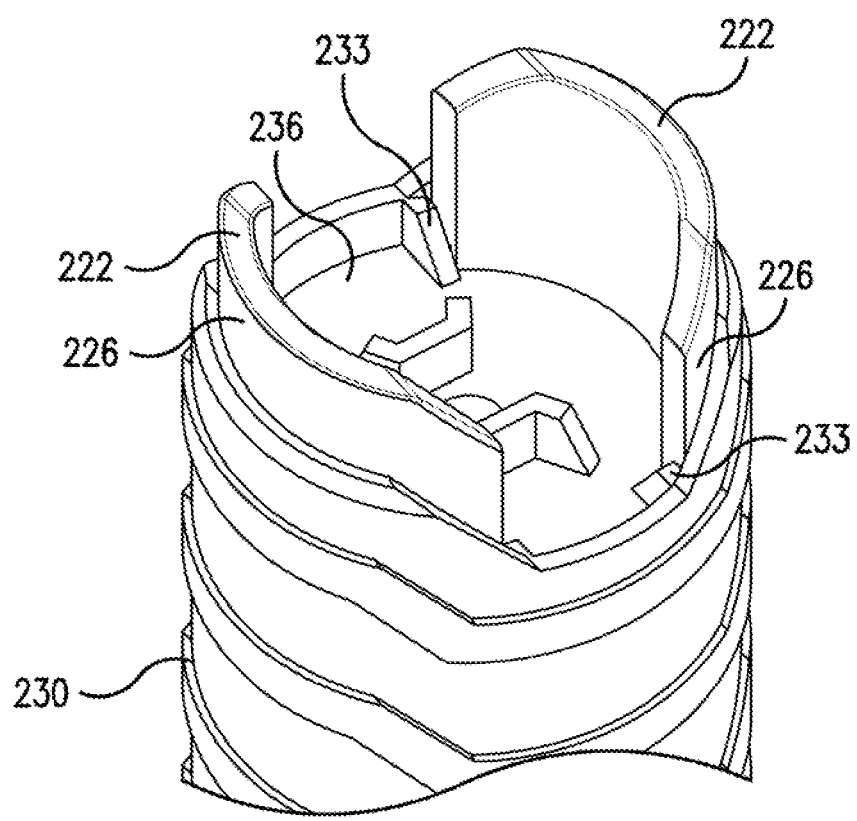
FIG. 13 is a partial perspective view of an activation shell and activation guard according to various aspects of the invention.

Distal groove 242 can at least partially surround an activation guard radial protrusion 228 that extends along at least a portion of an outer surface of activation guard 220 in circumferential direction 50. Radial protrusion 228 can extend circumferentially along an entire outer surface of activation guard 220. In one aspect, distal groove 242 and radial protrusion 228 can permit rotation of activation shell 230 about activation guard 220. In an alternate aspect, rotation of activation shell 230 about activation guard 220 can be prevented such that activation guard 220 and activation shell 230 rotate together about activation housing 210. As shown in FIG. 13, for example, rotation between activation shell 230 and activation guard 220 can be prevented by the interface of activation shell inward protrusions 233 with guard members 226.

Activation guard 220 can extend beyond the proximal end 232 of activation shell 230 such that when autoinjector device 10 is improperly oriented, activation guard 220 can be the first portion of autoinjector device 10 that comes into contact with the user. As such, activation of autoinjector device 10 can be prevented from actuating when improperly oriented. In an alternate aspect of the invention, the activation guard 220 can be integrally formed with activation housing 210 at its proximal end 212 such that guard members 226 can extend beyond proximal end 232 of activation shell 230.

Activation guard 220 can include one or more guard members 226 that can extend beyond proximal end 232 of activation shell 230. In another aspect, guard members can be integrally formed with activation housing 210 at proximal end 212 and can extend beyond proximal end 232 of activation shell 230.

Activation guard 220 can be assembled onto activation housing 210 by placing activation guard distal end 224 over activation housing proximal end 212 and sliding distal end 224 toward activation housing distal end 214 until distal surface 225 abuts shoulder 218 and/or groove 229 surrounds radial protrusion 216.

After activation guard 220 is assembled onto activation housing 210, the activation engine including piston 208, retaining element 206, pushing mechanism 204, and detent projections 202 can be placed into activation housing 210.

Figure 9:
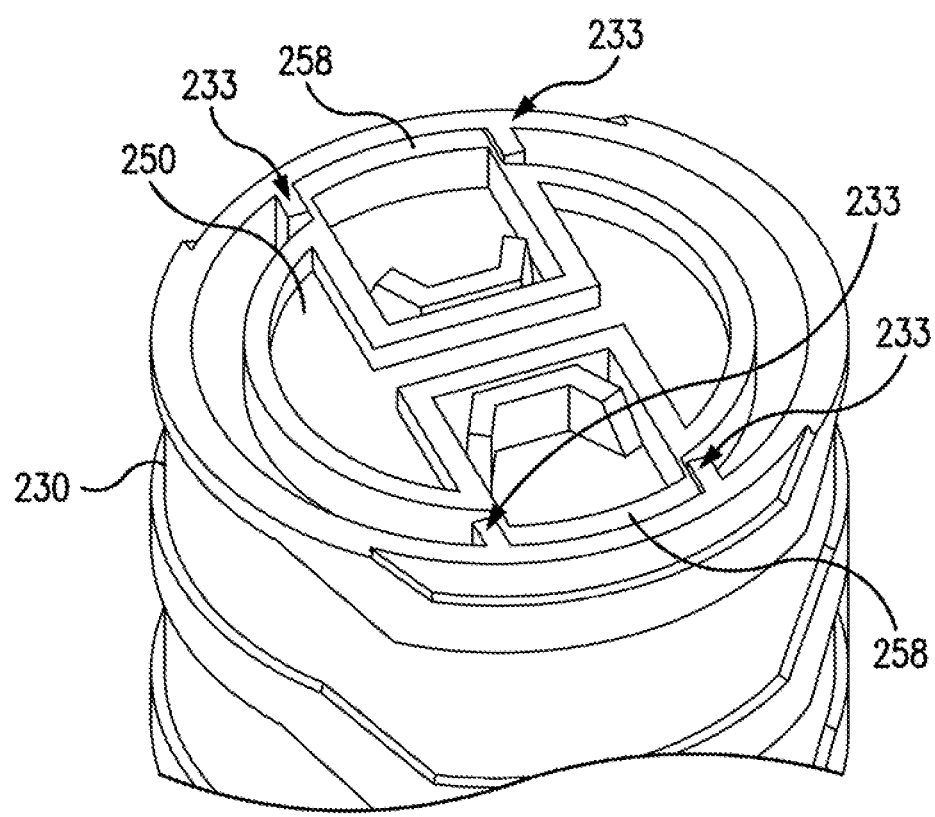
FIG. 9 is partial perspective view of an activation shell and device lock according to various aspects of the invention.

Referring now to FIGS. 5-6, device lock 250 can be maintained in position on activation shell 230 at activation shell proximal end 232 to prevent the activation shell 230 from moving and activating the autoinjector 10. For example, device lock 250 can include a radial protrusion 256 that couples with activation shell proximal groove 240 to hold device lock 250 in place on activation shell 230. As shown in FIG. 9, rotation between activation shell 230 and device lock 250 can be prevented by the interface of activation shell inward protrusions 233 with device lock tabs 258.

Activation shell 230 can be assembled onto activation guard 220 by placing activation shell distal end 234 over activation guard proximal end 222 and sliding distal end 234 toward activation guard distal end 224 until distal groove 242 surrounds radial protrusion 228. Device lock 250 can then be placed over the activation shell proximal end 232 and activation guard proximal end 222 to secure the activation shell 230 and prevent it from moving axially toward distal end 14 to activate the autoinjector 10.

FIGS. 1 and 7 show activator unit 200 in a storage position. In this state, pushing mechanism 204, shown in FIGS. 7-8 as a pretensioned coil spring, can be in a tensioned state between a piston 208 at the distal end and device lock 250 at its proximal end. To maintain the storage position, retaining element 206 can hold piston 208 in position using detent projections 202 that can in turn engage a holding disk 203 arranged in the region of proximal end 12 of autoinjector device 10. The holding disk 203 can be made of a metallic material and can include a coating to improve the strength of the holding disk 203 and, therefore, reduce the probability that the holding disk 203 becomes deformed or distorted from the force excreted by the pushing mechanism 204. In one example, the coating is a metal coating, such as a metal from Group 10 through Group 12 of the Periodic Table of Elements. For example, the coating can be from Group 10 of the Periodic Table of Elements. An example of such a coating is a nickel coating. In the storage position, detent projections 202 can be maintained in position against holding disk 203 by device lock central pin 251. Device lock central pin 251 can extend into an interior area of detent projections 202. Thus, device lock central pin 251 can prevent freedom of movement of detent projections 202, in particular, inward deformation during application of an axial force to activation shell 230. Device lock central pin 251 can extend through device lock hole 252 in proximal surface 236 of activation shell 230. Furthermore, the device lock 250 secures the activation shell 230 in a position so that it cannot axially move and activate the autoinjector 10.

When device lock 250 is removed and autoinjector device 10 is oriented properly, application of force along axial direction 30 toward distal end 14 can cause a relative displacement of the activation shell 230 relative to the activation housing 210. Through this displacement, detent projections 202 displace radially inwards, and can release from holding disk 203. As detent projections 202 release, pushing mechanism 204 can apply pressure to piston 208 which can move distally toward distal end 14 and can puncture film-type seal 107. Piston 208 can then come into contact with pressure pin 105 which can move distally toward distal end 14. Pressure pin 105 can press cartridge 104 against needle 102, thus connecting cartridge 104 and needle 102.

After cartridge 104 and needle 102 are connected, pressure pin 105, cartridge 104 along with the drug, and needle 102 can move distally by the pressure applied by pushing mechanism 204. Needle 102 can then penetrate into a user's body part.

In one example, the force necessary along axial direction 30 toward distal end 14 to cause a relative displacement of the activation shell 230 can be from about 0.1 lb. to about 40 lbs., such as from about 1 lb. to about 30 lbs., from about 5 lbs. to about 20 lbs. or from about 10 lbs. to about 15 lbs.

Should a user improperly orient autoinjector device 10, activation guard 220 can abut the user's body part and prevent activation of autoinjector device 10. For example, activation guard 220 can prevent an application of force along axial direction 30 toward distal end 14 that would cause a relative displacement of the activation shell 230 relative to the activation housing 210. In addition, activation shell 230 can be prevented from moving toward proximal end 12 of autoinjector device 10 because distal end 244 of distal groove 242 abuts radial protrusion 228. The positioning of distal end 244 against radial protrusion 228 only allows activation shell 230 to move toward distal end 14 for activation of autoinjector device 10.

Figure 14:
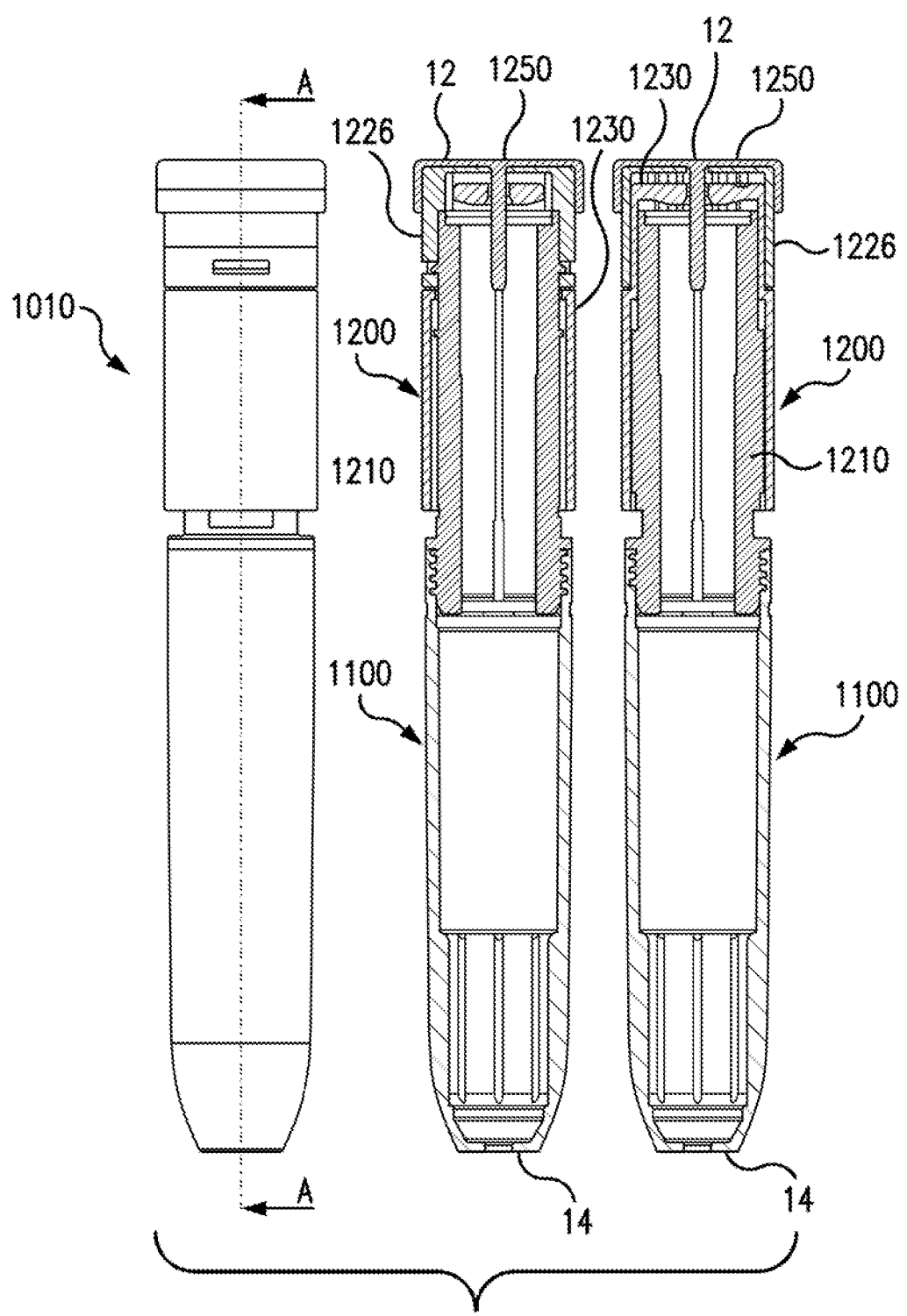
FIG. 14 is a front view and sectional view of an autoinjector device and activator unit according to an alternate aspect of the invention.
Figure 15:
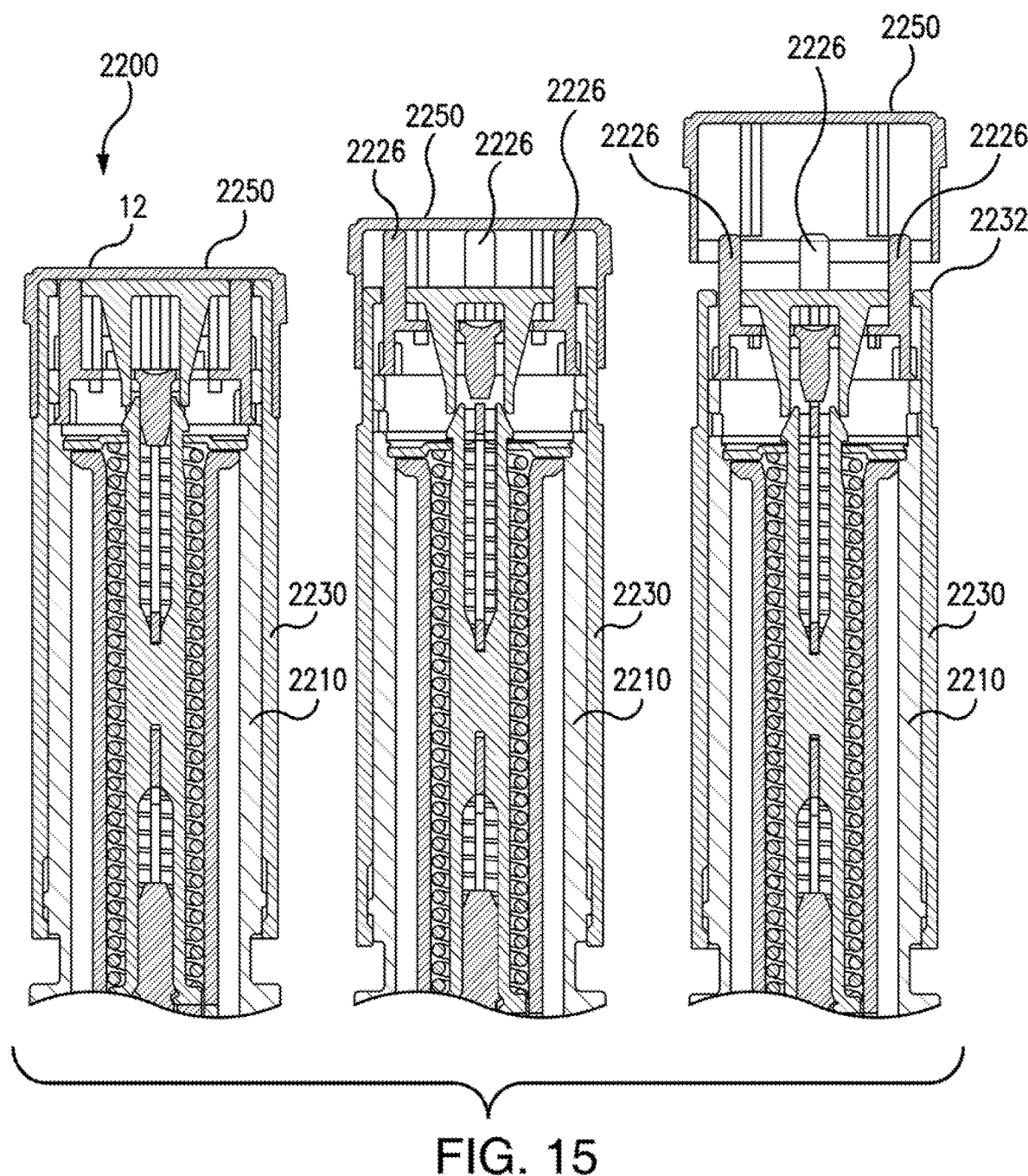
FIG. 15 is a sectional view of an activation housing, activation guard, and activation shell according to an alternate aspect of the invention.

FIGS. 14 and 15 illustrate additional autoinjector embodiments, with like numerals corresponding to similar features in FIGS. 1-13, described above. As shown in FIG. 14, autoinjector device 1010 can have a proximal end 12 and a distal end 14. Autoinjector device 1010 can include an injection unit 1100 at its distal end 14 and an activator unit 1200 at its proximal end 12. Activator unit 1200 can include an activation housing 1210, an activation guard 1226, an activation shell 1230, an activation engine within activation housing 1210, and a device lock 1250. In this aspect, activation guard 1226 can extend across proximal end 12. In a further aspect, activation guard 1226 can be fixed directly to activation housing 1210. In another aspect, activation guard 1226 can be integrally formed with activation housing 1210.

As shown in FIG. 15, Activator unit 2200 can include an activation housing 2210, activation guard members 2226, an activation shell 2230, an activation engine within activation housing 2210, and a device lock 2250. In this aspect, activation guard members 1226 can include one or more members that extend from proximal end 12. Activation guard members 2226 can extend beyond proximal surface 2232 of activation shell 2230. In a further aspect, activation guard members 2226 can be fixed directly to activation housing 2210. In another aspect, activation guard members 2226 can be integrally formed with activation housing 2210.

It is to be appreciated that the Detailed Description section, and not the Summary and Abstract sections, is intended to be used to interpret the claims. The Summary and Abstract sections may set forth one or more but not all exemplary embodiments of the present invention(s) as contemplated by the inventor(s), and thus, are not intended to limit the present invention(s) and the appended claims in any way.

The present invention(s) have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention(s) that others can, by applying knowledge within the skill of the art, readily modify and/or adapt for various applications such specific embodiments, without undue experimentation, without departing from the general concept of the present invention(s). Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention(s) should not be limited by any of the above-described exemplary embodiments, but should be defined only in accordance with the following claims and their equivalents.

What is claimed is:

1. An autoinjection device comprising:
    an injection unit defining a distal end of the autoinjection device; and
    an activator unit defining a proximal end of the autoinjection device, the activator unit comprising:
        an activation housing;
        an activation engine positioned within an interior area of the activation housing, the activation engine including a spring, a piston, and a retaining element, wherein the retaining element is configured to receive a portion of the piston within a distal end thereof;
        an activation guard at least partially surrounding the activation housing such that a portion of the activation housing is positioned within an interior area of the activation guard, wherein the activation guard includes at least one guard member that extends beyond a proximal end of the activation housing;
        an activation shell at least partially surrounding the activation guard such that a portion of the activation guard is positioned within an interior area of the activation shell, wherein the at least one guard member of the activation guard is extended beyond a proximal end of the activation shell; and
        a device lock positioned on a proximal end of the activator unit, the device lock including a locking mechanism configured to be positioned within a proximal end of the retaining element of the activation engine when the autoinjection device is in a storage position.

2. The autoinjection device of claim 1, wherein at least one of the activation housing, the activation guard, and the activation shell is substantially cylindrical in shape.

3. The autoinjection device of claim 1, wherein the activation housing includes a radial protrusion, and wherein the activation guard includes a groove proximate a distal end thereof that at least partially surrounds the activation housing protrusion such that through interaction therebetween the activation guard is prevented from linearly translating relative to the activation housing.

4. The autoinjection device of claim 3, wherein the activation guard includes a radial protrusion proximate the distal end thereof, and wherein the activation shell includes a linear groove surrounding the activation guard protrusion such that a distal end of the linear groove abuts the radial protrusion of the activation guard.

5. The autoinjection device of claim 1, wherein the device lock includes at least one radial ridge along an exterior surface thereof that is configured to be gripped by a user.

6. The autoinjection device of claim 1, wherein the activation shell includes a ridge on its outer surface to provide a user with a visual indication as to the distal end of the autoinjection device that includes a needle.

7. The autoinjection device of claim 1, wherein a proximal surface of the activation shell includes a camouflage to obscure a device lock protrusion opening.

8. The autoinjection device of claim 7, wherein the camouflage is a camouflage structure.

9. The autoinjection device of claim 1, wherein a distal surface of the activation guard abuts a shoulder of the activation housing.

10. The autoinjection device of claim 1, wherein in the storage position a proximal end of the at least one guard member of the activation guard is disposed proximate the device lock.

\* \* \* \* \*